US00PP34754P2

(12) United States Plant Patent
Lazzeri

(10) Patent No.: US PP34,754 P2
(45) Date of Patent: Nov. 22, 2022

(54) ***MANDEVILLA* PLANT NAMED 'LVDIP1816'**

(50) Latin Name: *Mandevilla hybrida*
Varietal Denomination: LVDIP1816

(71) Applicant: Carlo Lazzeri, Vacaria (BR)

(72) Inventor: Carlo Lazzeri, Vacaria (BR)

( * ) Notice: Subject to any disclaimer, the term of this patent is extended or adjusted under 35 U.S.C. 154(b) by 0 days.

(21) Appl. No.: 17/829,294

(22) Filed: May 31, 2022

Related U.S. Application Data

(60) Provisional application No. 63/197,795, filed on Jun. 7, 2021.

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Mandevilla* plant named 'LVDIP1816', characterized by its upright to outwardly spreading and semi-trailing plant habit; moderately vigorous to vigorous growth habit; early and freely flowering habit; single bright red-colored flowers; and good container performance.

2 Drawing Sheets

Figure 1:
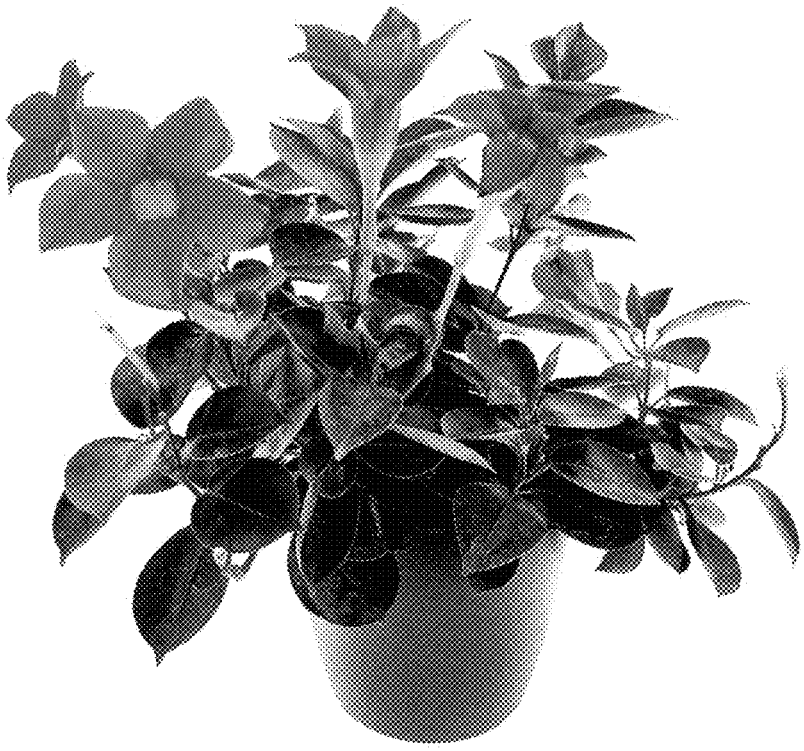

Botanical designation: *Mandevilla hybrida.*
Cultivar denomination: 'LVDIP1816'.

STATEMENT REGARDING PRIOR DISCLOSURES BY INVENTOR/APPLICANT

An European Plant Breeder's Rights application for the instant plant was filed by the Inventor/Applicant on Jun. 7, 2021, application number 2021/1469. Foreign priority is not claimed to this application.

BACKGROUND OF THE INVENTION

The present invention relates to a new and distinct cultivar of *Mandevilla* plant, botanically known as *Mandevilla hybrida* and hereinafter referred to by the name 'LVDIP1816'.

The new *Mandevilla* plant is a product of a planned breeding program conducted by the Inventor in Vacaria, Brazil. The objective of the breeding program is to develop new strong and freely flowering *Mandevilla* plants with attractive flowers and good garden performance.

The new *Mandevilla* plant originated from a cross-pollination in 2017 in Vacaria, Brazil of *Mandevilla hybrida* 'Fisrix Hopink' (trade name, Rio Hot Pink), disclosed in U.S. Plant Pat. No. 20,672, as the female, or seed, parent with *Mandevilla hybrida* 'Sunmandecrim', disclosed in U.S. Plant Pat. No. 15,539, as the male, or pollen, parent. The new *Mandevilla* plant was discovered and selected by the Inventor as a single flowering plant from within the progeny of the stated cross-pollination grown in a controlled greenhouse environment in Vacaria, Brazil in November, 2018.

Asexual reproduction of the new *Mandevilla* plant by terminal stein cuttings in a controlled environment in Vacaria, Brazil since January, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LVDIP1816'. These characteristics in combination distinguish 'LVDIP1816' as a new and distinct *Mandevilla* plant:

1. Upright to outwardly spreading and semi-trailing plant habit.
2. Moderately vigorous to vigorous growth habit.
3. Early and freely flowering habit.
4. Single bright red-colored flowers that resist fading.
5. Good container performance.

Plants of the new *Mandevilla* can be compared to plants of the female parent, 'Fisrix Hopink'. Plants of the new *Mandevilla* differ primarily from plants of 'Fisrix Hopink' in the following characteristics:

1. Plants of the new *Mandevilla* have larger flowers than plants of 'Fisrix Hopink'.
2. Plants of the new *Mandevilla* have bright red-colored flowers whereas plants of 'Fisrix Hopink' have rose red to cherry red-colored flowers.

Plants of the new *Mandevilla* can be compared to plants of the male parent, 'Sunmandecrim'. Plants of the new *Mandevilla* differ primarily from plants of 'Sunmandecrim' in the following characteristics:

1. Plants of the new *Mandevilla* are more upright than plants of 'Sunmandecrim'.

2. Plants of the new *Mandevilla* have lighter-colored flower throats than plants of 'Sunmandecrim'.
3. Flowers of plants of the new *Mandevilla* resist fading with development whereas flowers of plants of 'Sunmandecrim' fade with development.

Plants of the new *Mandevilla* can also be compared to plants of *Mandevilla sanderi* 'Fisrix Dered', disclosed in U.S. Plant Pat. No. 20,714. In side-by-side comparisons, plants of the new *Mandevilla* differ primarily from plants 'Fisrix Dered' in the following characteristics:

1. Plants of the new *Mandevilla* are more vigorous than plants of 'Fisrix Dered'.
2. Plants of the new *Mandevilla* have larger leaves than plants of 'Fisrix Dered'.
3. Plants of the new *Mandevilla* have bright red-colored flowers whereas plants of 'Fisrix Dered' have more scarlet-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'LVDIP1816' grown in a container.

Figure 2:
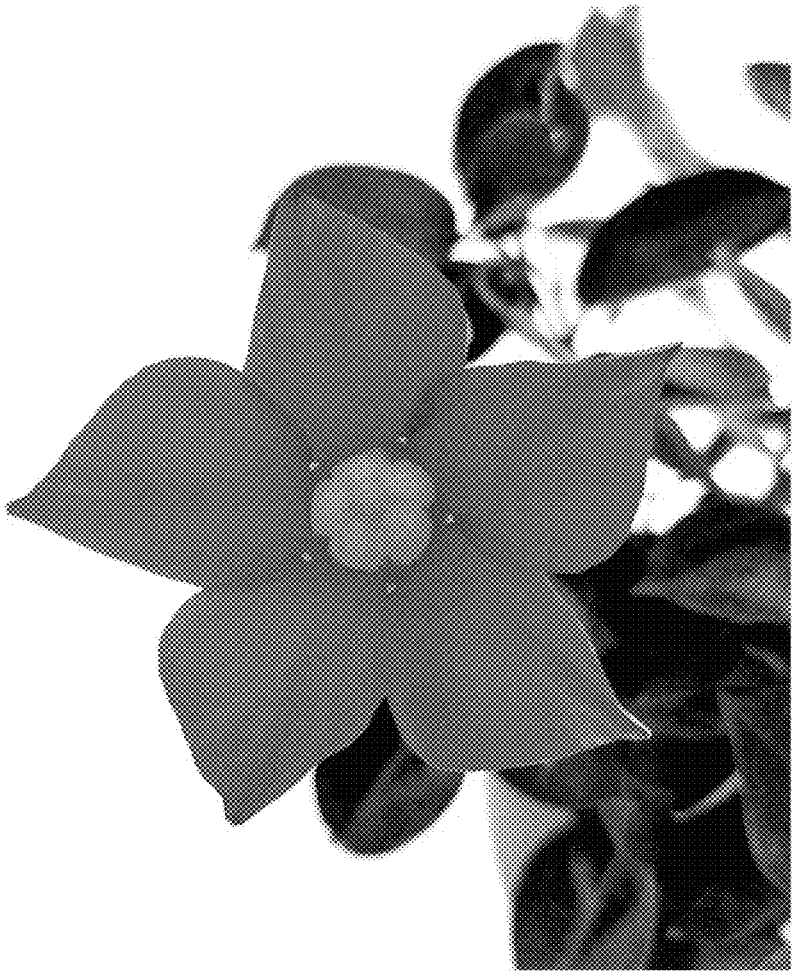

The photograph on the second sheet (FIG. 2) is a close-up view of a typical flower of 'LVDIP1816'.

DETAILED BOTANICAL DESCRIPTION

The aforementioned photographs and following observations, measurements and values describe plants grown during the summer in 10.5-cm containers in a polyethylene-covered greenhouse in Merano, Italy and under cultural practices typical of commercial *Mandevilla* production. During the production of the plants, day temperatures ranged from 20° C. to 28° C. and night temperatures ranged from 10° C. to 18° C. Plants were 20 weeks old when the photographs and description were taken. In the following description, color references are made to The Royal Horticultural Society Colour Chart, 2015 Edition, except where general terms of ordinary dictionary significance are used.

Botanical classification: *Mandevilla hybrida* 'LVDIP1816'.

Parentage:

*Female, or seed, parent.*—*Mandevilla hybrida* 'Fisrix Hopink', disclosed in U.S. Plant Pat. No. 20,672.

*Male, or pollen, parent.*—*Mandevilla hybrida* 'Sunmandecrim', disclosed in U.S. Plant Pat. No. 15,539.

Propagation:

*Type.*—By vegetative cuttings.

*Time to initiate roots, summer.*—About three weeks at temperatures about 25° C.

*Time to initiate roots, winter.*—About four weeks at temperatures about 14° C.

*Time to produce a rooted young plant, summer.*—About five weeks at temperatures about 25° C.

*Time to produce a rooted young plant, winter.*—About six weeks at temperature about 14° C.

*Root description.*—Thin, fibrous; typically creamy white in color, actual color of the roots is dependent on substrate composition, water quality, fertilizers, substrate temperature and physiological age of roots.

*Rooting habit.*—Freely branching; medium density.

Plant description:

*Plant and growth habit.*—Upright to outwardly spreading and semi-trailing plant habit; roughly broadly obovate in overall shape; moderately vigorous to vigorous growth habit and moderate growth rate.

*Plant height, soil level to top of foliar plane.*—About 28.5 cm.

*Plant height, soil level to top of floral plane.*—About 29.1 cm.

*Plant diameter (spread).*—About 32.4 cm.

*Lateral branch description.*—Branching habit: Freely branching habit, typically about three primary lateral branches each with about two secondary lateral branches. Length: About 16.8 cm. Diameter: About 2.25 mm. Internode length: About 2.5 cm. Aspect: Primary lateral branches, mostly upright; secondary lateral branches, about 15° to 60° from primary branch axis. Strength: Strong. Texture and luster: Smooth, glabrous; slightly glossy; becoming woody with development. Color, developing: Close to 143B. Color, developed: Close to a blend of 143B and 143C; when woody, close to N199B and 200D.

Leaf description:

*Arrangement.*—Opposite or in whorls of three, simple.

*Length.*—About 6 cm.

*Width.*—About 4 cm.

*Shape.*—Broadly ovate to broadly obovate.

*Apex.*—Apiculate to abruptly acute.

*Base.*—Truncate to rounded.

*Margin.*—Entire.

*Texture and luster, upper and lower surfaces.*—Smooth, glabrous; moderately coriaceous; moderately glossy.

*Venation pattern.*—Pinnate.

*Color.*—Developing leaves, upper surface: Close to 143A to 143B. Developing leaves, lower surface: Close to 147B tinged with close to 197A. Full expanded leaves, upper surface: Slightly darker than a blend of NN137A and 147A; venation, close to 144A. Fully expanded leaves, lower surface: Close to 146B; venation, close to 145A.

*Petioles.*—Length: About 1 cm. Diameter: About 2 mm by 2 mm. Strength: Moderately strong. Texture and luster, upper and lower surfaces: Smooth, glabrous; slightly glossy. Color, upper surface: Close to 144A. Color, lower surface: Close to 144B.

Flower description:

*Flower type and flowering habit.*—Single salverform flowers arranged in terminal and axillary cymes; flowers face outwardly to slightly upright and slightly nodding; freely flowering habit with about six flowers per inflorescence and about 60 flower buds and open flowers developing per plant during the flowering season.

*Natural flowering season.*—Plants flower continuously from spring into the autumn in Italy; plants begin flowering about 45 days after planting rooted young plants.

*Flower longevity on the plant.*—Individual flowers last about ten days; flowers not persistent.

*Fragrance.*—None detected.

*Inflorescence height.*—About 13 cm.

*Inflorescence diameter*.—About 11.1 cm.

*Flower buds*.—Length: About 5.7 cm. Diameter: About 1 cm. Shape: Narrowly oblanceolate. Texture and luster: Smooth, glabrous; slightly glossy. Color: Distally, slightly darker than 46A; proximally, close to 145B and tube, close to 144B.

*Flowers*.—Appearance: Flared trumpet, corolla fused and five-parted. Diameter: About 6.8 cm by 6.8 cm. Depth (length): About 6.5 cm. Throat diameter: About 1.4 cm. Tube length: About 4.4 cm. Tube diameter: Proximally, about 4 5 mm; distally, about 1.6 cm.

*Corolla*.—Quantity and arrangement: Five petals arranged in a single whorl; lower 57% portion of the petals are fused into a funnelform tube. Petal length: About 7.7 cm. Petal width: About 2.5 cm. Petal shape and appearance: Roughly unequal spatulate; slightly convex. Petal apex: Apiculate, unequal. Petal margin: Entire; slightly and coarsely undulate. Petal texture and luster, upper surface: Smooth, glabrous; velvety; slightly glossy. Petal texture and luster, lower surface: Smooth, glabrous; slightly velvety; moderately glossy. Throat texture: Smooth, glabrous; velvety. Tube texture: Smooth, glabrous; slightly velvety. Color: Petal, when opening, upper surface: Close to N45A. Petal, when opening, lower surface: Close to 46A; towards the apex, tinged with close to 56D. Petal, fully opened, upper surface: Close to N45A; towards the apex, tinged with close to 46A; venation, similar to lamina color; color does not change with subsequent development. Petal, fully opened, lower surface: Close to 53B; towards the apex, flushed with close to N155B; midvein, close to 47B; color does not change with subsequent development. Throat: Close to 24A; at the base of the throat, close to 151C to 151D; venation, similar to lamina colors. Tube: Distally, close to 53B and proximally, close a blend of 145C and 150D; at the base, close to 144C; venation, similar to lamina colors.

*Sepals*.—Quantity and arrangement: Five sepals arranged in a single whorl. Length: About 7 mm. Width: About 1.5 mm. Shape: Lanceolate. Apex: Narrowly acuminate. Base: Broadly cuneate and fused. Margin: Entire. Texture and luster, upper surface: Smooth, glabrous; moderately glossy. Texture and luster, lower surface: Smooth, glabrous; matte. Color: When developing, upper and lower surfaces: Close to 145D; towards the base, close to 144B; towards the apex, close to 184C. Fully developed, upper and lower surfaces: Close to 145D; towards the base, close to 144B; towards the apex, slightly tinged with close to 184B.

*Peduncles*.—Length: About 7.2 cm. Diameter: About 2 mm. Strength: Strong. Aspect: About 30° from lateral branch axis. Texture and luster: Smooth, glabrous; moderately glossy. Color: Close to 143A.

*Pedicels*.—Length: About 1.6 cm. Diameter: About 2 mm. Strength: Strong. Aspect: About 20° to 60° from peduncle axis. Texture and luster: Smooth, glabrous; moderately glossy. Color: Close to 144B.

*Reproductive organs*.—Stamens: Quantity and arrangement: Typically five; basifixed; anthers connivent. Filament length: About 2 mm. Filament color: Close to 151D. Anther shape: Narrowly oblong. Anther size: About 1.75 mm by 9 mm. Anther color: Close to 160C. Pollen amount: None observed. Pistils: Quantity: Typically one. Pistil length: About 2.3 cm. Style length: About 2.1 cm. Style color: Close to 150D. Stigma diameter: About 1.75 mm. Stigma shape: Club-shaped, pointed. Stigma color: Close to 148C. Ovary color: Close to 144A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'LVDIP1816' as illustrated and described.

* * * * *